United States Patent [19]

Sih

[11] Patent Number: 5,587,318

[45] Date of Patent: *Dec. 24, 1996

[54] PROCESS FOR PREPARING(S)-α-METHYLARYLACETIC ACIDS

[75] Inventor: Charles I. Sih, Madison, Wis.

[73] Assignee: Wisconsin Alumni Research Foundation, Madison, Wis.

[*] Notice: The term of this patent shall not extend beyond the expiration date of Pat. No. 5,322,791.

[21] Appl. No.: 215,285

[22] Filed: Mar. 21, 1994

Related U.S. Application Data

[62] Division of Ser. No. 879,538, May 4, 1992, Pat. No. 5,322,791, which is a continuation of Ser. No. 518,285, May 4, 1990, abandoned, which is a continuation of Ser. No. 942,149, Dec. 16, 1986, abandoned, which is a continuation-in-part of Ser. No. 840,280, Mar. 17, 1986, abandoned, which is a continuation-in-part of Ser. No. 811,260, Dec. 20, 1985, abandoned.

[51] Int. Cl.$^6$ .............................. C12P 7/40; C12P 7/54; C12N 1/14
[52] U.S. Cl. ..................... 435/280; 435/136; 435/141; 435/921; 435/255.4
[58] Field of Search ................................. 435/136, 280, 435/141, 189, 921, 255.4

[56] References Cited

U.S. PATENT DOCUMENTS

| | | |
|---|---|---|
| 4,601,987 | 7/1986 | Kilbanov et al. . |
| 4,668,628 | 5/1987 | Dahod et al. . |
| 4,762,793 | 8/1988 | Cesti et al. . |

OTHER PUBLICATIONS

Charles J. Sih et al, "Resolution of Enantiomers via Biocatalysis", Topics in Stereochemistry, 1989, vol. 19, pp. 63–125.

Ching–Shih et al, "Quantitative Analyses of Biochemical Kinetic Resolution of Enantiomers. 2. Enzyme–Catalyzed Esterifications in Water–Organic Solvent Biphasic Systems", Journal of the American Chemical Society, 1987, vol. 109, pp. 2812–2817.

Qu–Ming Gu et al, "A Facile Enzymatic Resolution Process for the Preparation of (+)–S–2–(6–Methoxy–2–Naphthyl) Propionic Acid (Naproxen)", Tetrahedron Letters, 1986 vol. 27, No. 16, pp. 1763–1766.

Bernard Cambou et al, "Lipase–Catalyzed Production of Optically Active Acids via Asymmetric Hydrolysis of Esters", Applied Biochemistry and Biotechnology, 1984, vol. 9, pp. 255–260.

Bernard Cambou et al, "Comparison of Different Strategies for the Lipase–Catalyzed Preparative Resolution of Racemic Acids and Alcohols: Asymmetric Hydrolysis, Esterification, and Transesterification", Biotech. and Bioeng., 1984, vol. 26, pp. 1449–1454.

William D. Wilson, "Enantioselective Hydrolysis of 3–Hydroxy–3–methylalkanoic Acid Esters with Pig Liver Esterase", Journal of Org. Chem., 1983, vol. 48, No. 22, pp. 3960–3966.

Ching–Shih, "Quantitative Analysis of Biochemical Kinetic Resolutions of Enantiomers", Journal of the American Chemical Society, 1982, vol. 104, No. 25, pp. 7294–7299.

Shinobu Iriuchijma et al, "Asymmetric Hydrolysis of (+/–)–α–Substituted Carboxylic Acid Esters with Microorganisms", Agric. Biol. Chem., 1981, pp. 1389–1392.

M. Bodansky et al, "Peptide Synthesis", Interscience, 1966, Chapter V, pp. 98–109.

*Primary Examiner*—Irene Marx
*Attorney, Agent, or Firm*—Andrus, Sceales, Starke & Sawall

[57] ABSTRACT

The invention relates to a process for preparing (S)-α-methylarylacetic acids from mixtures, such as racemic mixtures, of (R)- and (S)-α-methylarylacetic acid esters by enantiospecific hydrolysis using extracellular lipases of microbial origin (EC 3.1.1.3).

12 Claims, No Drawings

PROCESS FOR PREPARING(S)-α-METHYLARYLACETIC ACIDS

CROSS-REFERENCE TO RELATED APPLICATIONS

This application is a division of Ser. No. 07/879,538 filed May 4,1992, now U.S. Pat. No. 5,322,791, which is in turn a continuation of Ser. No. 07/518,285 filed May 4,1990, now abandoned, which is in turn a continuation of Ser. No. 06/942,149 filed Dec. 16, 1986, now abandoned, which in turn is a continuation-in-part of my commonly-assigned application, Ser. No. 06/840,280, filed Mar. 17, 1986, entitled "Process for Preparing Optically-Active 2-Aryl-Propionic Acids", now abandoned, which is in turn a continuation-in-part of my commonly-assigned application, Ser. No. 06/811,260, filed Dec. 20, 1985, entitled "Process for Preparing Optically-Active 2-(6-Methoxy-2-Naphthyl)Propionic Acid", now abandoned. Both of these latter two applications are incorporated herein by reference.

BACKGROUND OF THE INVENTION

1. Field of the Invention

This invention relates to processes for producing chiral α-methylarylacetic acids. More specifically, it relates to a process for preparing (S)-α-methylaryl-acetic acids from mixtures, such as racemic mixtures, of (R)- and (S)-α-methylarylacetic acid esters by enantiospecific hydrolysis using extracellular lipases of microbial origin (EC 3.1.1.3).

2. Background to the Invention

A number of α-methylarylacetic acids (2-arylpropionic acids) are known as antiinflammatory agents: among the best known being ibuprofen, flurbiprofen, ketoprofen, and suprofen (all of which are substituted α-methylbenzeneacetic acids), and naproxen (a substituted α-methylnaphthaleneacetic acid). As is well known, the α-methylarylacetic acid molecule is chiral at the α-carbon atom and, therefore, exists in two stereoisomeric forms: the R- and S-forms (these forms are named by application of the "Sequence Rule", see *J. Org. Chem.*, 35, 2863–7 (1970)). The S-enantiomers of these α-methylarylacetic acids generally possess greater antiinflammatory activity than the R-enantiomers ["Non-steroidal Antiinflammatory Drugs", J. G. Lombardino (ed.), John Wiley & Sons, New York, 1985, p. 303]. For example, the S-enantiomer of 6-methoxy-α-methyl-2-naphthaleneacetic acid has 28 times greater antiinflammatory activity than the R-enantiomer [I. T. Harrison et al., *J. Med. Chem.*, 13, 203 (1970)]. Hence, the S-enantiomer alone is used as the antiinflammatory drug naproxen (USAN and the USP Dictionary of Drug Names, 1986, p. 222).

The chemical synthesis of 6-methoxy-α-methyl-2-naphthaleneacetic acid [I. T. Harrison et al., *J. Med. Chem.*, 13, 203 (1970)] leads to a racemic mixture of R- and S-enantiomers. Hence, resolution methods have to be employed to obtain the separate enantiomers from the racemic mixture. These resolution methods are, however, cumbersome and expensive. Generally, the chemical resolution methods entail the selective stoichiometric crystallization of a diastereomeric salt by the use of an expensive amine such as cinchonidine [P. Wirth et al., German Pat. (Offen.) 2,319,245 (1973); U.S. Pat. Nos. 3,787,580; 3,651,106; 3,906,038] or dehydroabietylamine acetate [British Pat. 1,426,186 (1976)], or the use of a water soluble amine such as glucamine, which is difficult to recover [E. Felder et al., U.K. Pat. App. 2025968A (1980)]. Naproxen has also been prepared by the chemical resolution of a precursor using the expensive and less-available (1)-10-camphor-sulfonic acid [G. I. Tsuchihashi, *Tet. Lett.*, 5427 (1982)].

Various microbiological techniques have been reported for the preparation of chiral α-methylaryl-acetic acids. For example, the intact microorganism of *Aspergillus sojae* was used for the partial resolution of (±)-6-methoxy-α-methyl-2-naphthaleneacetic acid methyl ester [S. Iriuchijima and A. Keiyu, *Agri. Biol. Chem.*, 45, 1389 (1981)]. Unfortunately, the rate of conversion was very slow (only 16.3% of the substrate was converted), because the intracellular enzyme concentration was low and the amount of dried cells (400 mg) exceeded the amount of (±)-ester substrate (160 mg), and the R-isomer, rather than the desired S-isomer, of the acid was produced. Boehringer Mannheim GmbH, in European Pat. App. 153474, describe the enantioselective enzymatic hydrolysis of (±)-6-methoxy-α-methyl-2-naphthaleneacetic acid (using, e.g., esterases from *Aspergillus oryzae*, *Aspergillus flavus*, *Aspergillus sojae*, and *Bacillus subtilis*) to produce the R-isomer of the acid, leaving the S-ester. The S-ester is then hydrolyzed with an esterase from hog liver or *Pleurotus ostreatus* to give the desired S-acid. Montedison S.p.A., in European Pat. App. 195717, describe the enantioselective hydrolysis of certain (±)-α-arylalkanoic acid esters to produce the S-acids, using a lipase from *Candida cylindracea*, a lipase which is exemplified in my prior applications.

SUMMARY OF THE INVENTION

This invention relates to a process for preparing an (S)-α-methylarylacetic acid from a substrate comprising a mixture, such as a racemic mixture, of (R)- and (S)-α-methylarylacetic acid esters by enantiospecific hydrolysis using an extracellular lipase of microbial origin (EC 3.1.1.3).

DETAILED DESCRIPTION OF THE INVENTION

The α-methylarylacetic acid esters which are the substrates for the enantiospecific hydrolysis are of the general formula:

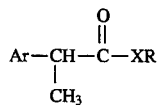

wherein:

Ar is an optionally substituted aryl group;

X is oxygen or sulfur; and

R is an optionally substituted alkyl group.

Ar is preferably a monocyclic, polycyclic, or condensed polycyclic aromatic or heteroaromatic group having up to 12, preferably 6 to 12, carbon atoms in the aromatic system, such as phenyl, biphenyl, naphthyl, thienyl, and pyrrolyl. The aromatic group is optionally substituted with one or more nitro, halo, hydroxy, $C_{1-4}$ alkyl, $C_{3-6}$ cycloalkyl, benzyl, $C_{1-4}$ alkoxy, $C_{1-4}$ alkylthio, $C_{1-4}$ haloalkyl, $C_{1-4}$ haloalkoxy, phenoxy, thenoyl, and benzoyl groups.

Specific examples of aryl groups, Ar, suitable for the purposes of the present invention are phenyl, 4-benzoylphenyl, 4-isobutylphenyl, 4-(2-thenoyl)phenyl, 3-fluorobiphenyl, 6-methoxy-2-naphthyl, 5-halo-6-methoxy-2-naphthyl, 6-hydroxy-2-naphthyl, and 5-halo-6-hydroxy-2-naphthyl.

X is preferably oxygen.

R is preferably a straight, branched, or cyclic alkyl group having from 1 to 12 carbon atoms, optionally substituted with phenyl or one or more electron-withdrawing substituents, for example halo, nitro, cyano, hydroxy, $C_{1-4}$ alkoxy, $C_{1-4}$ alkylthio, or —C(O)$R^1$ wherein $R^1$ is $C_{1-4}$ alkyl, $C_{3-6}$ cycloalkyl, hydroxy, $C_{1-4}$ alkoxy, $C_{3-6}$ cycloalkoxy, phenoxy, benzyloxy, $NR^2R^3$ [in which $R^2$ and $R^3$ are independently H, $C_{1-4}$ alkyl, $C_{3-6}$ cycloalkyl, or jointly form a 5- or 6-membered ring together with the nitrogen, the ring optionally including a hetero group selected from O, NH, or N-($C_{1-4}$ alkyl)], or —OM wherein M is an alkali metal.

The electron-withdrawing substituents if present are preferably at the α- or β-position of the R group, to the extent consistent with the stability of the group. Esters in which the R groups contain electron-withdrawing substituents are referred to as activated esters, since they generally hydrolyse more rapidly than those where the R group is not so substituted.

Specific examples of alkyl groups, R, are methyl, ethyl, butyl, hexyl, octyl, dodecyl, benzyl, 2-chloroethyl, 2,2,2-trichloroethyl, 2-fluoroethyl, 2,2,2-trifluoroethyl, 2-bromoethyl, cyanomethyl, 2-nitropropyl, carboethoxymethyl, methoxymethyl, 2-hydroxy-1,2-dimethoxycarbonylethyl, 2-hydroxy-1,2-dicarboxyethyl, 2-hydroxy-1,2-diethoxycarbonylethyl, etc.

Starting Materials and Purification

The esters of the (R)- and (S)-α-methylarylacetic acids which are to be resolved can be prepared by conventional methods (see, e.g., I. T. Harrison and S. Harrison in "Compendium of Organic Synthetic Methods", Chapter 8, Wiley, N.Y., 1971, page 271). Indeed, conventional (non-enantiospecific) syntheses of α-methylarylacetic acids and their esters typically produce racemic, or approximately racemic, mixtures of the R- and S-isomers, so that the substrates for the enantiospecific hydrolysis of this invention are readily available.

If the resulting (S)-α-methylarylacetic acid is a precursor of a drug such as naproxen, for example (S)-5-halo-6-methoxy-α-methyl-2-naphthaleneacetic acid, (S)-6-hydroxy-α-methyl-2-naphthaleneacetic acid or (S)-5-halo-6-hydroxy-α-methyl-2-naphthaleneacetic acid, such precursor can be converted to naproxen by methods described in European Published Application 95901 (1983).

The (S)-α-methylarylacetic acids which are the product of the process of this invention may be purified by conventional chemical means, typically by recrystallization from an organic solvent; and characterized by physical and spectral properties, such as melting point, optical rotation, and the like.

Enantiospecific Hydrolysis

The process of the invention comprises subjecting the substrate comprising the mixture of (R)- and (S)-α-methylarylacetic acid esters to the hydrolytic enzymatic action of an extracellular microbial lipase (EC 3.1.1.3) and recovering the desired (S)-α-methylarylacetic acid.

It has been found that extracellular microbial lipases are capable of functioning to catalyze enantiospecific hydrolysis. Particularly suitable are those extracellular lipases derived from the microorganisms of the genera Candida, Rhizopus, Mucor, Aspergillus, Penicillium, Pseudomonas, Chromobacterium, and Geotrichium. Particularly preferred is the lipase of *Candida cylindracea* [N. Tomizuka et al., Agri. Biol. Chem., 30, 576 (1966)].

Extracellular microbial lipases are well known and many of these are available commercially [see, e.g. M. Iwai and Y. Tsujisaka, p. 443, and M. Sugiura, p. 505, in "Lipases," ed. B. Borgström and H. L. Brockman, Elsevier, N.Y., 1984]. For example, they are used industrially for the transesterification of fats and were incorporated in laundry detergents for removal of oily contaminants. One outstanding feature of these lipases that distinguishes them from intact microorganisms is that they can tolerate high substrate and product concentrations. For example, no marked substrate and product inhibition were noted. Hence, these enzymatic hydrolytic reactions can be carried out in high concentrations (0.1–5 M) with an unusually high degree of enantiospecificity. Moreover, they are remarkably stable under the described reaction conditions, so that they may be recovered from reaction media (e.g. by filtration on a membrane filter or similar methods) and reused.

The microorganisms producing these lipases may be grown on a liquid nutritional soil according to conventional procedures, for example, by inoculating the microorganism into a sterilized liquid culture medium and causing to grow on an alternating shaker at between 20° C. and 40° C. for a period of 1–3 days.

Suitable lipase concentrations are those conventional in the art, and are largely determined by experiment based on the desired rate of conversion compared to the lipase cost. For the *Candida cylindracea* lipase, which has a molecular weight of approximately 100,000, suitable concentrations are about $10^{-5}$ M to $10^{-3}$ M, typically about $10^{-4}$ M or 10 mg/mL of pure lipase.

The mixture of (R)- and (S)-α-methylarylacetic acid esters constituting the substrate may be added in solid or liquid forms at concentrations of 0.1–5 M, typically 1–2 M, to a liquid medium containing the lipase to effect the enantiospecific hydrolysis. The liquid medium can be water, the same culture broth of the microorganism, or its extracts or concentrates, or the suspensions of the microorganism cells. Alternatively, the substrate can be dissolved in a suitable organic solvent such as carbon tetrachloride, cyclohexane, carbon disulfide, or hexane, as long as the solvent does not denature the lipase. In addition, the substrate may be emulsified by the use of emulsifying agents such as polyvinyl alcohol or propylene glycol. Of course, the time and temperature and pressure conditions for the contact of the substrate with the lipase are interdependent, as will be apparent to those skilled in the art. Generally, at atmospheric pressure, the temperature can range from about 10° C. to about 40° C., and is preferably at the upper end of that range (e.g. 25°–40° C.) for maximum conversion rate. The pH of the medium can range from about 3 to about 8, typically from about 4 to about 7, and is preferably maintained relatively constant, e.g. by addition of acid or base or through the use of a buffer solution such as phosphate buffer. The time for the reaction is typically between a few hours and a few weeks, say 4 hours to 3 weeks, and more typically is between about 2 and 7 days. This time can be substantially varied by variation of the temperature and pressure of the reaction, and by the concentration of substrate and lipase, as well as by the nature of the substrate and lipase themselves, and optimization of such conditions may be performed by techniques known to the art.

Following the enantiospecific hydrolysis reaction, the α-methylarylacetic acid enriched in the S-form and the unreacted ester enriched in the R-form may be extracted from the reaction mixture by using water-immiscible organic solvents such as ethyl acetate, methylene chloride, ethyl ether and toluene and the like. Subsequently, the acid enriched in the S-form and the ester enriched in the R-form can be separated by extraction or chromatography.

Alternatively, the α-methylarylacetic acid enriched in the S-form may be isolated by extraction using aqueous alkaline solutions such as aqueous solutions of sodium hydroxide or potassium hydroxide.

The separation of the S-acid and the R-ester may also be accomplished by centrifuging or filtering the reaction mixture to isolate the solid which is the R-ester. Acidifying the supernatant or the filtrate will give the desired S-acid.

It will be obvious to those skilled in the art that the process of this invention as set forth hereinbefore can be modified and perhaps improved by various means.

For example, the process may be made continuous wherein the lipase is immobilized (e.g. on water-soluble or water-insoluble polymers, inorganic materials such as diatomaceous earth, etc.) by conventional techniques [see, e.g., "Immobilized Enzymes", M. D. Trevan, Wiley, N.Y., 1980] and recycled several times to reduce cost; the R-ester can be recovered, racemized [see, e.g., J. Kenyon and D. P. Young, J. Chem. Soc., 216 (1940)] and reused; or the substrate can be exposed to the lipase as a microcrystalline powder to obtain better dispersion. Furthermore, it may be possible to dissolve the substrate and a racemization agent in a suitable solvent so only the ester will be continuously racemized in situ without cleaving the ester grouping. In such case, this process would be tantamount to an asymmetric synthesis. Also, activators and stabilizers of the lipase, such as surfactants (e.g. bile acids, phospholipids) or emulsifiers, in low concentration, [see, e.g., N. Tomizuka et al., Agri. Biol. Chem., 30, 576 (1966)] may be introduced to the mixture, or activated ester substrates [Bodansky et al., Peptide Synthesis, 2nd Ed., Wiley, N.Y., 1976, pp. 99–108] may be used to enhance the rate of conversion. In addition, active site directed mutagenesis or chemical modification of the lipase may be used to prepare lipases with improved catalytic efficiency, $V_{max}/K_m$, ["Enzymatic Reaction Mechanisms", C. Walsh, Freeman, N.Y., 1979, p. 35] and/or stability.

EXAMPLES

The following examples are presented to illustrate this invention and are not to be considered as limiting the scope of the appended claims.

EXAMPLE 1

To a suspension of *Candida cylindracea* lipase (100 mg) (Sigma L1754 Type VII, 500 units/mg solid) in 1 mL 0.2 M phosphate buffer, pH 8.0, were added 244 mg (±)-6-methoxy-α-methyl-2-naphthaleneacetic acid methyl ester as a fine powder, giving a 1 M suspension of the racemic ester substrate, and 100 mg polyvinyl alcohol (MW 14,000). The reaction mixture was stirred with a magnetic stirrer for 6 days at 24° C. The contents were then acidified with HCl and exhaustively extracted with ethyl acetate three times. The combined organic extract was dried over sodium sulfate and was then evaporated to dryness. The residue was suspended in 5% aqueous NaHCO$_3$ and extracted with hexane to obtain unreacted (R)-6-methoxy-α-methyl-2-naphthaleneacetic acid methyl ester (128 mg), $[\alpha]_D^{23}$=−41.35° (c=5.34, CHCl$_3$). Acidification of the aqueous layer with HCl to pH 2.0, followed by extraction with dichloromethane, gave 58 mg (S)-6-methoxy-α-methyl-2-naphthaleneacetic acid, $[\alpha]_D^{23}$=+65.0° (c=1.64, CHCl$_3$).

EXAMPLES 2–7

The general procedure of Example 1 was repeated except that the different esters of (±)-6-methoxy-α-methyl-2-naphthaleneacetic acid tabulated below were used as substrates. In each case, (S)-6-methoxy-α-methyl-2-naphthaleneacetic acid was obtained in good yield, with the optical activity shown.

| Example | Ester | $[\alpha]_D^{23}$ |
| --- | --- | --- |
| 2 | ethyl | +64.2°(c = 0.59, CHCl$_3$) |
| 3 | n-butyl | +64.3°(c = 0.6, CHCl$_3$) |
| 4 | n-hexyl | +64.7°(c = 1.2, CHCl$_3$) |
| 5 | n-octyl | +63.6°(c = 1.8, CHCl$_3$) |
| 6 | n-dodecyl | +59.8°(c = 1.3, CHCl$_3$) |
| 7 | benzyl | +61.6°(c = 0.9, CHCl$_3$) |

EXAMPLE 8

The general procedure of Example 1 was repeated except that *Candida cylindracea* lipase immobilized on celite (as described by Y. Kimura et al., Eur. J. Appl. Microbiol. Biotechnol., 17, 107 (1983)) was used as the lipase to obtain (S)-6-methoxy-α-methyl-2-naphthalene-acetic acid in good yield, $[\alpha]_D^{23}$=+60.18° (c=1.1, CHCl$_3$).

EXAMPLE 9

The general procedure of Example 1 was repeated except that *Candida cylindracea* lipase (Sigma) immobilized on acrylic beads [K. Laumen et al., Tet. Lett., 407 (1985)] was used as the lipase to obtain (S)-6-methoxy-α-methyl-2-naphthaleneacetic acid, $[\alpha]_D^{25}$=+63.8° (c=1.2, CHCl$_3$).

EXAMPLE 10

The general procedure of Example 1 was repeated except that 2500 units *Chromobacterium viscosum* lipase (Type XII, Sigma) was used as the lipase to obtain optically active 6-methoxy-α-methyl-2-naphthalene-acetic acid.

EXAMPLE 11

The general procedure of Example 1 was repeated except that 10 mg *Pseudomonas* lipo-protein Lipaic 80 (Amano, 800 u/gm) was used as the lipase to obtain optically active 6-methoxy-α-methyl-2-naphthalene-acetic acid.

EXAMPLE 12

The general procedure of Example 1 was repeated except that 10 mg purified *Geotrichium candidum* (ATCC 34614) lipase [Y. Tsujisaka et al., Agr. Biol. Chem., 37, 1457 (1973)] was used as the lipase to obtain optically active 6-methoxy-α-methyl-2-naphthaleneacetic acid.

EXAMPLE 13

The general procedure of Example 1 was repeated except that 200 mg crude lipase of *Penicillium cyclopium* ATCC 34613 [H. Iwai et al., Agr. Biol. Chem., 39, 1063 (1975)] was used as the lipase to obtain optically active 6-methoxy-α-methyl-2-naphthaleneacetic acid.

EXAMPLE 14

To 10 mg purified *Candida cylindracea* lipase (1100 units/mg) [N. Tomizuka et al., Agr. Biol. Chem., 30, 576 (1966)] in 1 mL of 0.2 M phosphate buffer, pH 8.0, was added 244 mg (±)-6-methoxy-α-methyl-2-naphthaleneacetic acid methyl ester as a fine powder, giving a 1 M suspension. The resulting suspension was gently stirred with a magnetic stirrer for 5 days at 22° C. The reaction mixture was then centrifuged for 5 min at 1000×g. The precipitate was washed once with 0.2 M phosphate buffer, pH 8.0, and again centrifuged to collect the unreacted water-insoluble (R)-6-methoxy- α-methyl-2-naphthaleneacetic acid methyl ester (94 mg), $[\alpha]_D^{23}=-72.39°$ (c=6.98, CHCl$_3$). The supernatant and the washings were combined and acidified to pH 2.5 with 3 N HCl and the precipitate was collected by centrifugation to yield 96 mg (S)-6-methoxy-α-methyl-2-naphthaleneacetic acid, $[\alpha]_D^{23}=+68.87°$ (c=5.22, CHCl$_3$).

EXAMPLE 15

To 50 mg crude *Candida cylindracea* lipase (Sigma L1754 Type VII, 500 units/mg solid) in 1 mL 0.2 M phosphate buffer, pH 8.0, were added 292 mg (±)-6-methoxy-α-methyl-2-naphthaleneacetic acid 2-chloroethyl ester as a fine powder, giving a 1 M suspension, $1\times10^{-3}$ M mercaptoethanol, and 10 mg polyvinyl alcohol. The resulting suspension was gently stirred with a magnetic stirrer for 42 hours at 22° C. The reaction mixture was then centrifuged for 5 min at 1000×g and the precipitate was washed with 0.2 M phosphate buffer, pH 8.0, and again centrifuged to collect the unreacted water-insoluble (R)-6-methoxy-α-methyl-2-naphthaleneacetic acid 2-chloroethyl ester (140 mg), $[\alpha]_D^{23}=-20.5°$ (c=4.96, CHCl$_3$). The supernatant and the washings were combined and acidified to pH 2.0 with 3 N HCl and the precipitate was collected by filtration to afford 92 mg of (S)-6-methoxy-α-methyl-2-naphthaleneacetic acid, $[\alpha]_D^{23}=+64.2°$ (c=3.49, CHCl$_3$).

EXAMPLE 16

To 10 mg *Candida cylindracea* lipase (Meito Sangyo Lipase OF-360, 360,000 u/g) in 1 mL 0.2 M phosphate buffer, pH 8.0, were added 292 mg (±)-6-methoxy-α-methyl-2-naphthaleneacetic acid 2-chloroethyl ester as a fine powder, giving a 1 M suspension, $1\times10^{-3}$ M mercaptoethanol, and 10 mg polyvinyl alcohol. The resulting suspension was gently stirred with a magnetic stirrer for 48 hours at 22° C. The reaction mixture was then filtered, and the precipitate was washed with 0.2 M phosphate buffer, pH 8.0. The solid consisted of unreacted (R)-6-methoxy-α-methyl-2-naphthaleneacetic acid 2-chloroethyl ester (120 mg), $[\alpha]_D^{25}=-16.51°$ (c=7.73, CHCl$_3$). The filtrate and the washings were combined and acidified to pH 2.0 with 3 N HCl and the precipitate was collected by filtration to give 66 mg (S)-6-methoxy-α-methyl-2-naphthaleneacetic acid, $[\alpha]_D^{25}=+61.18°$ (c=3.3, CHCl$_3$).

EXAMPLES 17–24

The general procedure of Example 16 was repeated except that the different esters of (±)-6-methoxy-α-methyl-2-naphthaleneacetic acid were used as substrates to obtain (S)-6-methoxy-α-methyl-2-naphthaleneacetic acid.

| Example | Ester | $[\alpha]_D^{23}$ |
|---|---|---|
| 17 | 2,2,2-trichloroethyl | +67.0°(c = 1.25, CHCl$_3$) |
| 18 | cyanomethyl | +67.07°(c = 2.59, CHCl$_3$) |
| 19 | 2-nitropropyl | +61.8°(c = 5.2, CHCl$_3$) |
| 20 | 2-bromoethyl | +60.8°(c = 4.1, CHCl$_3$) |
| 21 | carboethoxymethyl | +62.07°(c = 3.18, CHCl$_3$) |
| 22 | methoxymethyl | +63.28°(c = 2.17, CHCl$_3$) |
| 23 | 2-fluoroethyl | +62.81°(c = 3.84, CHCl$_3$) |
| 24 | 2,2,2-trifluoroethyl | +61.87°(c = 4.13, CHCl$_3$) |

EXAMPLE 25

To 100 mg crude *Candida cylindracea* lipase (Sigma L1754 Type VII, 500 units/mg solid) in 4 mL 0.2 M phosphate buffer, pH 7.0, was added 200 mg (±)-α-methyl-4-(2-thienylcarbonyl)benzeneacetic acid methyl ester (suprofen methyl ester). The resulting suspension was gently stirred with a magnetic stirrer for 48 hours at 22° C. The reaction mixture was acidified to pH 1.0 with 1 N HCl and exhaustively extracted with ethyl acetate three times. The combined organic extract was dried over sodium sulfate and was then evaporated to dryness. The residue was chromatographed over a silica gel (MN Kieselgel 60) column (0.8×15 cm). Elution of the column with a solvent system consisting of ethyl acetate-hexane (1:5) gave unreacted (R)-α-methyl-4-(2-thienylcarbonyl)benzeneacetic acid methyl ester, $[\alpha]_D^{25}=-54.7°$ (c=3.9, CHCl$_3$), ee>0.90, and (S)-α-methyl-4-(2-thienylcarbonyl)benzeneacetic acid, $[\alpha]_D^{25}=+43.5°$ (c=2.1, CHCl$_3$), ee>0.95. The optical purity expressed as enantiomeric excess (ee) is determined by proton magnetic resonance spectroscopy of the methyl ester in the presence of the chiral lanthanide shift reagent, Eu(hfc)$_3$.

EXAMPLE 26

The general procedure of Example 25 was repeated except that 200 mg of (±)-α-methyl-4-(2-methylpropyl)-benzeneacetic acid methyl ester (ibuprofen methyl ester) was used as the substrate. Unreacted (R)-α-methyl-4-(2-methylpropyl)benzeneacetic acid methyl ester, $[\alpha]_D^{25}=-45.1°$ (c=5.3, CHCl$_3$), ee=0.70, and (S)-α-methyl-4-(2-methylpropyl)benzeneacetic acid, $[\alpha]_D^{25}=+50.44°$ (c=2.7, CHCl$_3$), ee=0.95, were recovered.

EXAMPLE 27

The general procedure of Example 25 was repeated except that 200 mg of (±)-α-methylbenzeneacetic acid methyl ester was used as the substrate. Unreacted (R)-α-methylbenzeneacetic acid methyl ester, $[\alpha]_D^{25}=-67.8°$ (c=2.2, CHCl$_3$), ee=0.80, and (S)-α-methylbenzeneacetic acid, $[\alpha]_D^{25}=+27.4°$ (c=2.0, CHCl$_3$), ee=0.45, were recovered.

EXAMPLE 28

The general procedure of Example 25 was repeated except that 200 mg (±)-2-fluoro-α-methyl-[1,1'-biphenyl]-4-acetic acid methyl ester (flurbiprofen methyl ester) was used as the substrate and 100 mg *Candida cylindracea* lipase (Meito Sangyo Lipase OF-360, 360,000 u/g) as the lipase. Unreacted (R)-2-fluoro-α-methyl-[1,1'-biphenyl]-4-acetic acid methyl ester, $[\alpha]_D^{25}=-21.5°$ (c=4.8, CHCl$_3$), ee=0.41, and (S)-2-fluoro-α-methyl-[1,1'-biphenyl]-4-acetic acid, $[\alpha]_D^{25}=+29.7°$ (c=2.3, CHCl$_3$), ee=0.65, were recovered.

EXAMPLE 29

The general procedure of Example 25 was repeated except that 200 mg (±)-3-benzoyl-α-methylbenzene-acetic acid methyl ester (ketoprofen methyl ester) was used as the substrate and 100 mg *Candida cylindracea* lipase (Meito Sangyo Lipase OF-360, 360,000 u/g) as the lipase. Unreacted (R)-3-benzoyl-α-methylbenzeneacetic acid methyl ester, $[\alpha]_D^{25}=-43.8°$ (c=1.6, CHCl$_3$), ee=0.60, and (S)-3-benzoyl-α-methyl-benzeneacetic acid, $[\alpha]_D^{25}=+34.3°$ (c=3.5, CHCl$_3$), ee=0.60, were recovered.

I claim:

1. A process for preparing (S)-6-methoxy-α-methyl-2-naphthaleneacetic acid which comprises subjecting a substrate comprising a mixture of (R)- and (S)-6-methoxy-α-methyl-2-naphthaleneacetic acid esters, said esters selected from the group consisting of 2,2,2-trichloroethyl, cyanomethyl, 2-nitropropyl, 2-chloroethyl, methyl and 2-bromoethyl esters, to the hydrolytic enzymatic action of an extracellular microbial lipase isolated from *Candida cylindracea*, separating the unreacted (R)-6-methoxy-α-methyl-2-naphthaleneacetic acid ester, and recovering the (S)-6-methoxy-α-methyl-2-naphthaleneacetic acid.

2. The process of claim 1 wherein the mixture is a racemic mixture.

3. The process of claim 2 wherein the substrate is (±)-6-methoxy-α-methyl-2-naphthaleneacetic acid methyl ester.

4. The process of claim 2 wherein the substrate is (±)-6-methoxy-α-methyl-2-naphthaleneacetic acid 2-chloroethyl ester.

5. The process of claim 1 wherein the lipase is Meito Sangyo Lipase OF-360.

6. A process for preparing the S-isomer of an α-methylarylacetic acid from a substrate comprising a mixture of R- and S-isomers of esters of the α-methylarylacetic acid selected from the group consisting of (±)-α-methyl-4-(2-methylpropyl)benzeneacetic acid 2-chloroethyl ester, (±)-2-fluoro-α-methyl-(1,1'-biphenyl)-4-acetic acid 2-chloroethyl ester, (±)-3-benzoyl-α-methylbenzeneacetic acid 2-chloroethyl ester, and (±)-α-methyl-4-(2-thienylcarbonyl)benzeneacetic acid 2-chloroethyl ester, which comprises subjecting the substrate to enantiospecific hydrolysis using an extracellular lipase isolated from *Candida cylindracea* and recovering the S-isomer of the α-methylarylacetic acid.

7. The process of claim 6 wherein the mixture of R- and S-isomers of esters of the α-methlarylacetic acid is a racemic mixture.

8. The process of claim 6 wherein the lipase is immobilized.

9. The process of claim 6 wherein the substrate is (±)-α-methyl-4-(2-methylpropyl)benzeneacetic acid 2-chloroethyl ester.

10. The process of claim 6 wherein the substrate is (±)-2-fluoro-α-methyl-(1,1'-biphenyl)-4-acetic acid 2-chloroethyl ester.

11. The process of claim 6 wherein the substrate is (±)-3-benzoyl-α-methylbenzeneacetic acid 2-chloroethyl ester.

12. The process of claim 6 wherein the substrate is (±)-α-methyl-4-(2-thienylcarbonyl)benzeneacetic acid 2-chloroethyl ester.

* * * * *